US00PP21835P2

(12) United States Plant Patent
Zaiger et al.

(10) Patent No.: US PP21,835 P2
(45) Date of Patent: Apr. 5, 2011

(54) CHERRY TREE NAMED 'ROYAL BAILEY'

(50) Latin Name: *Prunus avium*
Varietal Denomination: Royal Bailey

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/590,161

(22) Filed: Nov. 4, 2009

(51) Int. Cl.
*A01H 5/00* (2006.01)

(52) U.S. Cl. ..... Plt./181

(58) Field of Classification Search ..... Plt./181
See application file for complete search history.

*Primary Examiner* — Susan B McCormick Ewoldt

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit maturing in the early season.
2. Regular production of large size fruit.
3. Fruit with good flavor and eating quality.
4. Fruit with an attractive red skin color.
5. Fruit remaining firm on the tree 7 to 10 days past maturity (shipping ripe).
6. Vigorous, upright tree growth.

1 Drawing Sheet

Botanical classification: *Prunus avium.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherries, which are known to us, and mentioned herein, 'Minnie Royal' Cherry (U.S. Plant Pat. No. 12,942) and 'Royal Dawn' Cherry (U.S. Plant Pat. No. 13,131).

STATEMENT REGARDING FEDERALLY SPONSORED RESEARCH AND DEVELOPMENT

Not applicable.

ORIGIN OF THE VARIETY

The present variety of cherry tree (*Prunus avium*) was developed by us in our experimental orchard located near Modesto, Calif. as an open pollinated seedling selected from our proprietary seedling with field identification number '22ZB383'. The seed parent (22ZB383) originated as a first generation cross between 'Royal Dawn' Cherry (U.S. Plant Pat. No. 13,131) and 'Minnie Royal' Cherry (U.S. Plant Pat. No. 12,942). A large number of these open pollinated seedlings were budded on established trees of 'Mahaleb' Rootstock (non-patented) to accelerate fruit production. Under close and careful observation, one such seedling, which is the present variety, having especially desirable fruit and tree characteristics was selected in 2003 for asexual reproduction and commercialization.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., shows that reproductions run true to the original tree and all characteristics of the tree and its fruit are established and transmitted through succeeding asexual propagations.

SUMMARY OF THE NEW VARIETY

The new and distinct variety of cherry tree is of large size, vigorous, upright growth and a regular and productive bearer of large, early maturing fruit with an attractive red skin color. The fruit is further characterized by its good flavor and eating quality, having firm fruit with good shipping and handling qualities that remains firm on the tree approximately 7 to 10 days past maturity (shipping ripe). In comparison to its seed parent (22ZB383) the fruit of the new variety ripens approximately 12 days earlier with larger sizes. In comparison to its ancestor 'Royal Dawn' Cherry (U.S. Plant Pat. No. 13,131) the fruit of the new variety is larger in size with a brighter red skin color. In comparison to its ancestor 'Minnie Royal' Cherry (U.S. Plant Pat. No. 12,942) the new variety blooms approximately 7 days later and produces larger size fruit ripening approximately 9 days later.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 10 year old tree and the colors are as nearly true as is reasonably possible in a color representation of this type.

DESCRIPTION OF THE VARIETY

The following is a detailed description of the new variety of cherry tree, its flowers, foliage and fruit, as based on observations of 10 year old specimens grown near Modesto, Calif., with color in accordance with Munsell Book of Color.

Tree:

*Size.*—Large. Average spread 3 meters. Average height 4 meters, varies with different cultural practices.

*Vigor.*—Vigorous. Tree growth reaching 1 to 2 meters the first growing season. Growth rate varies with soil type and depth, cultural practices and climatic conditions.

*Form.*—Upright, during the first and second growing seasons scaffolds are selected and tied down to increase crotch angle and help spread tree to the desired width.

*Branching habit.*—Upright. Crotch angle approximately 35° when juvenile, the weight of fruit tends to increase branch angle.

*Productivity.*—Productive, produces adequate fruit set annually.

*Bearer.*—Regular, adequate fruit set for 7 consecutive years.

*Fertility.*—Self sterile, pollinator required.

*Density.*—Medium dense. Normally pruned to vase shape to allow for air movement and sunlight to center of tree to enhance the health of fruit spurs and fruit color.

*Hardiness.*—Hardy in all stone fruit growing areas of California. Tree grown in USDA Hardiness Zone 9. Winter chilling requirement is approximately 750 hours at below 45° F.

Trunk:

*Size.*—Large. Average circumference of 87.6 cm at 26.7 cm above the ground on a 10 year old tree. Varies with climatic conditions, soil type and cultural practices.

*Stocky.*—Medium stocky.

*Texture.*—Medium rough, roughness increases with age.

*Color.*—Varies from 10YR 5/2 to 10YR 3/2.

Branches:

*Size.*—Medium. Average circumference of 14.9 cm at 1.2 meters above the ground.

*Surface texture.*—New growth smooth. Older growth medium rough, roughness increases with age.

*Lenticels.*—Average number of 16 in a 25.8 square cm section. Average length 6.2 mm. Average width 2.6 mm. Color varies from 10YR 5/8 to 10YR 5/10.

*Color.*—New growth varies from 5GY 5/6 to 5GY 5/8. Old growth varies from 5YR 3/2 to 7.5YR 2/4, varies with age of growth.

Leaves:

*Size.*—Large. Average length 159.7 mm. Average width 71.8 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins, glabrous. Lower surface relatively smooth except for ridges created by midrib and pinnate venation, glabrous.

*Petiole.*—Average length 37.2 mm. Average width 2.1 mm. Longitudinally grooved. Color varies from 5GY 4/6 to 7.5R 2/6.

*Glands.*—Reniform. Average length 3.0 mm. Average diameter 2.0 mm. Number varies from 1 to 3, average number 2. Located primarily on the upper portion of the petiole. Color varies from 7.5R 3/10 to 5GY 5/8.

*Color.*—Upper surface varies from 5GY 4/8 to 5GY 3/6. Lower surface varies from 5GY 4/4 to 5GY 4/6. Midvein color varies from 10Y 7/4 to 2.5GY 6/8.

Flower buds:

*Size.*—Large. Average length 17.0 mm. Average diameter 9.7 mm.

*Hardiness.*—Hardy with respect to California winters.

*Form.*—Plump to conical, becoming elongated before opening.

*Pedicel.*—Average length 10.5 mm. Average width 1.6 mm. Color varies from 2.5GY 6/8 to 5GY 6/6.

*Color.*—Varies from N 9.5/ (white) to 2.5R 8/4 on upper edge of petals.

*Number of buds per spur.*—Average 5, varies from 2 to 7.

Flowers:

*Blooming period.*—Date of First Bloom Mar. 10, 2009. Date of Petal Fall Mar. 20, 2009, varies slightly with climatic conditions.

*Size.*—Medium to large. Average height 19.7 mm. Average diameter 27.5 mm.

*Petals.*—Average 5, varies from 5 to 6 alternately arranged to the sepals. Average length 15.7 mm. Average width 15.5 mm. Orbicular, narrows at point of attachment. Margin — entire. Color — N 9.5/ (white).

*Sepals.*—Average 5, varies from 5 to 6 alternately arranged to the petals. Form — triangular. Margin — entire. Average length 6.8 mm. Average width 5.4 mm. Both surfaces glabrous. Color — upper surface varies from 2.5GY 6/6 to 5GY 6/6. Lower surface varies from 2.5GY 6/6 to 5GY 6/6 with 7.5R 4/6 on upper edges.

*Stamens.*—Number per flower 28 to 32. Average filament length 12.1 mm. Filament color N 9.5/ (white). Anther color varies from 5Y 8/8 to 5Y 8/10.

*Pollen.*—Self sterile, pollinator required. Color varies from 5Y 7/10 to 5Y 7/12.

*Pistil.*—Number per flower — usually one. Average length 14.3 mm. Position of stigma an average of 1.3 mm below anthers. Color varies from 2.5GY 7/6 to 2.5GY 7/8. Surface — glabrous.

*Fragrance.*—Very slight.

*Color.*—N 9.5/ (white).

*Number flowers per flower bud.*—Varies from 2 to 5, average 3.

*Pedicel.*—Average length 12.5 mm. Average width 1.6 mm. Color varies from 2.5GY 5/8 to 5GY 5/6.

Fruit:

*Maturity when described.*—Firm ripe.

*Date of first picking.*—May 10, 2009.

*Date of last picking.*—May 17, 2009, varies slightly with climatic conditions.

*Size.*—Large. Average diameter axially 25.7 mm. Average transversely in suture plane 26.1 mm. Average weight 14.2 grams, average weight varies slightly with fertility of the soil, amount of thinning and climatic conditions.

*Form.*—Broadly cordate.

*Suture.*—Nearly smooth, extends from base to apex.

*Ventral surface.*—Nearly rounded to very slightly lipped.

*Apex.*—Slightly retuse.

*Base.*—Retuse.

*Cavity.*—Rounded. Average depth 1.7 mm. Average diameter 6.1 mm.

Stem:

*Size.*—Large. Average length 44.7 mm. Average diameter 2.1 mm.

*Color.*—Varies from 2.5GY 4/4 to 10Y 5/4.

Flesh:

*Ripens.*—Evenly.

*Texture.*—Firm, crisp.

*Fibers.*—Few, small, tender.

*Firmness.*—Firm, comparable to 'Royal Dawn' Cherry (U.S. Plant Pat. No. 13,131).

*Aroma.*—Moderate.

*Amydgalin.*—Undetected.

*Eating quality.*—Very good.

*Flavor.*—Very good, a good balance between acid and sugar.

*Juice.*—Moderate amount, enhances flavor.

*Brix.*—Average 18.2°, varies slightly with amount of fruit per tree and climatic conditions.

*Color.*—Varies between 2.5Y 8.5/4 to 5R 3/8. Pit cavity varies from 5R 4/8 to 5R 3/8.

Skin:

*Thickness.*—Medium.

*Surface.*—Smooth.

*Pubescence.*—Wanting.

*Tendency to crack.*—None during dry weather. Slight tendency to crack during wet weather, varies with stage of maturity.

*Color.*—Varies from 5R 2/4 to 7.5R 2/8.

*Tenacity.*—Tenacious to flesh.

*Astringency.*—None.

Stone:

*Type.*—Clingstone.

*Size.*—Medium to large. Average length 12.2 mm. Average width 10.4 mm. Average thickness 8.7 mm.

*Form.*—Obovoid.

*Base.*—Flat.

*Apex.*—Rounded.

*Surface.*—Relatively smooth, very slightly pitted throughout.

*Sides.*—Varies from equal to unequal. Some stones having one side extending a greater distance from the suture plane.

*Ridges.*—Two small narrow ridges running along each of the suture.

*Tendency to split.*—None.

*Color.*—Varies from 10YR 7/4 to 10YR 7/6 when dry.

Kernel:

*Size.*—Large. Average length 7.9 mm. Average width 6.2 mm. Average depth 5.0 mm.

*Form.*—Ovoid.

*Viability.*—Viable, complete embryo development.

*Skin.*—Color varies from 5Y 9/4 to 7.5Y 9/4.

Use: Dessert. Market, local and long distance.

Keeping quality: Good, held well for 2 weeks at 38° to 42° F. and maintained good firmness and eating quality.

Shipping quality: Good, no excessive bruising or scarring in packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct cherry tree substantially as illustrated and described.

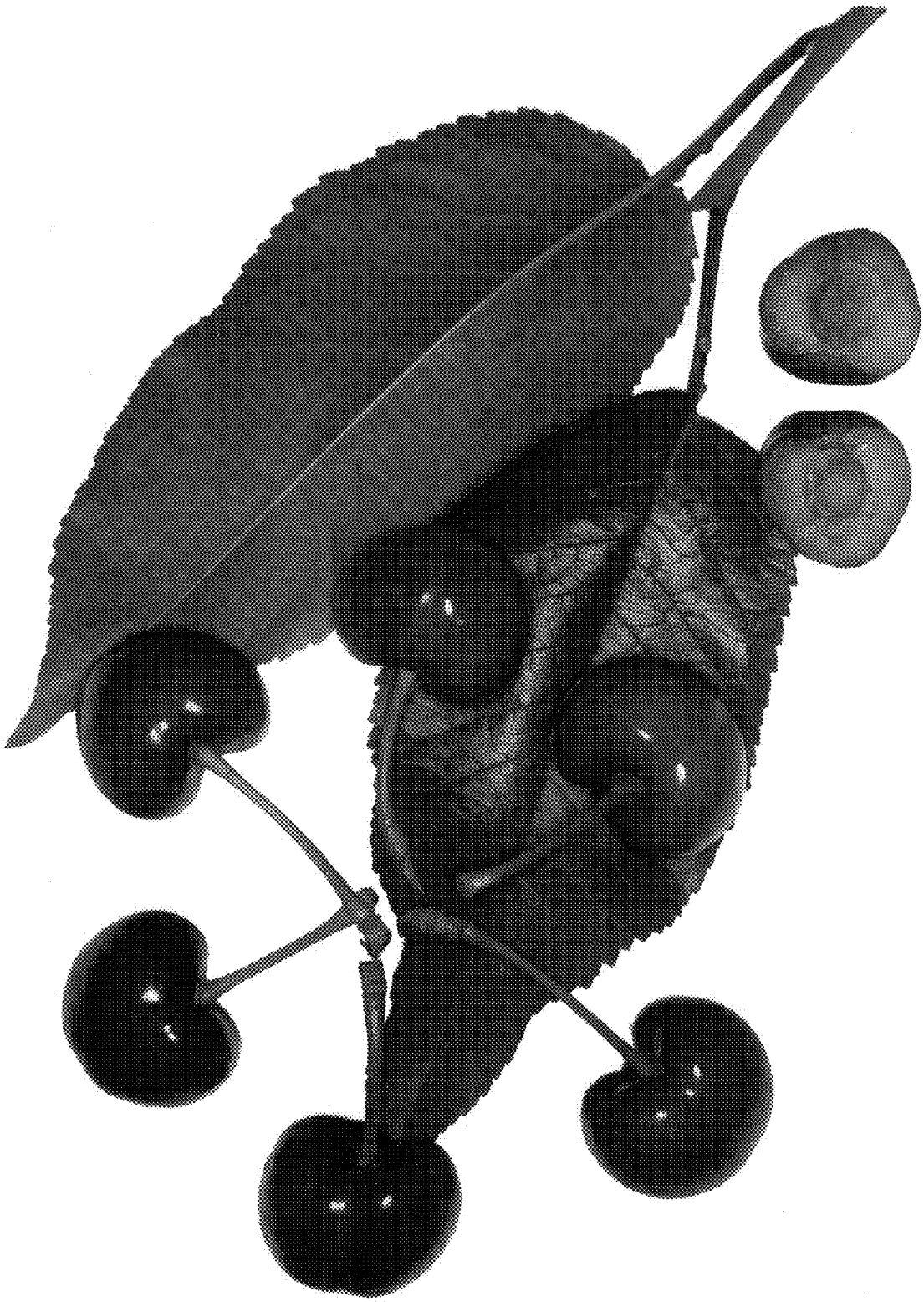

* * * * *